United States Patent [19]

Negus et al.

[11] Patent Number: 5,724,975
[45] Date of Patent: Mar. 10, 1998

[54] ULTRASONIC DETECTION SYSTEM FOR TRANSMYOCARDIAL REVASCULARIZATION

[75] Inventors: Charles Christopher Negus, Taunton; Eileen A. Woodruff, Millis; Robert I. Rudko, Holliston; Stephen J. Linhares, Taunton, all of Mass.

[73] Assignee: PLC Medical Systems, Inc., Franklin, Mass.

[21] Appl. No.: 764,052

[22] Filed: Dec. 12, 1996

[51] Int. Cl.⁶ ............................................. A61B 8/00
[52] U.S. Cl. ................. 128/661.09; 128/661.07; 128/660.03
[58] Field of Search .............. 128/661.07, 661.09, 128/662.04, 661.08, 660.03

[56] References Cited

U.S. PATENT DOCUMENTS

| | | | |
|---|---|---|---|
| 3,556,079 | 1/1971 | Omizo | 128/2 |
| 4,576,177 | 3/1986 | Webster, Jr. | 128/660.03 |
| 4,759,374 | 7/1988 | Kierney et al. | 128/661.09 |
| 5,105,815 | 4/1992 | Hall et al. | 128/661.08 |
| 5,119,821 | 6/1992 | Tuchler | 128/662.04 |
| 5,368,034 | 11/1994 | Isner | 128/660.03 |

*Primary Examiner*—Marvin M. Lateef
*Assistant Examiner*—Derrick Fields
*Attorney, Agent, or Firm*—Iandiorio & Teska

[57] ABSTRACT

An ultrasonic detection system for transmyocardial revascularization (TMR) is disclosed using a detector in the TMR handpiece for detecting concealed coronary blood vessels as well as verifying completion of transmural TMR channels by displaying the detector's output on a video monitor or analyzing the detector output electronically to identify those conditions.

17 Claims, 7 Drawing Sheets

ULTRASONIC DETECTION SYSTEM FOR TRANSMYOCARDIAL REVASCULARIZATION

FIELD OF INVENTION

This invention relates to an ultrasonic detection system for transmyocardial revascularization, and more particularly to such a system for detecting concealed coronary blood vessels and for detecting verification of completion of a transmyocardial revascularization channel.

BACKGROUND OF INVENTION

In conventional open heart transmyocardial revascularization (TMR) a channel is created through the heart wall from the outside to the inside of the left ventricle using a laser beam typically from a $CO_2$ laser. The channel heals quickly on the outside from light finger pressure so there is no substantial bleeding. The channel remains open on the inside part way through the heart wall so that the heart muscle is supplied with blood by suffusion through the channel from the ventricle. With a number of such channels the blood supply to the heart muscle can be restored to ensure proper functioning of the heart despite occluded coronary arteries. One problem encountered in TMR is the danger of creating a channel in a path which cuts an unseen vessel in the heart wall. When this occurs substantial bleeding can occur so that a stitch will be required on the outside of the channel at the heart wall to stanch the bleeding. In addition to the obvious danger and extra effort required, this technique also results in a less extensive channel. That is, channels which have such a stitch tend to heal for a longer distance into the heart wall thereby shortening the channel where the blood flows and reducing that area of the heart muscle suffused.

Another difficulty encountered in TMR is knowing that a transmural channel has penetrated completely through the heart wall so that the surgeon can be sure that blood suffusion of the heart muscle can take place and if not that the laser energy should be increased to ensure complete transmural channels.

SUMMARY OF INVENTION: I

It is therefore an object of this invention to provide an ultrasonic detection system for transmyocardial revascularization.

It is a further object of this invention to provide such an ultrasonic detection system for locating concealed coronary blood vessels in transmyocardial revascularization.

It is a further object of this invention to provide such an ultrasonic detection system for verifying completion of transmural channels in transmyocardial revascularization.

It is a further object of this invention to provide such an ultrasonic detection system which is simple, reliable and integratable with present transmyocardial revascularization.

The invention results from the realization that a truly safe, effective and reliable ultrasonic detection system for transmyocardial revascularization (TMR) can be achieved with a detector in the TMR handpiece that can detect concealed coronary blood vessels as well as verifying completion of transmural TMR channels by displaying the detector's output on a video monitor, for example, or analyzing the detector output electronically to identify those conditions.

This invention features an ultrasonic detection system for detecting concealed coronary blood vessels in transmyocardial revascularization. There is a handpiece and an ultrasonic detector in the handpiece. An indicator device responsive to the ultrasonic detector represents the presence of a coronary vessel concealed in the heart wall.

In a preferred embodiment the indicator may be mounted at the distal end of the handpiece. The indicator device may include an audio, visual or other form of display. The visual display may include a video monitor. The indicator device may include a signal processor circuit responsive to the detector for identifying the presence of a concealed coronary blood vessel. The signal processing unit may include a thresholding circuit to determine whether the output from the detector exceeds a predetermined level. The signal processing unit may also include a comparator circuit for comparing the periodicity of the detector output with that of the patient's heartbeat. The comparator circuit may include an EKG device.

The invention also features an ultrasonic detection system for detecting verification of a transmural laser created transmyocardial revascularization channel including a handpiece and an ultrasonic detector in the handpiece. An indicator device responsive to the ultrasonic detector represents the presence of a completed transmural channel.

In a preferred embodiment the detector may be mounted in the distal end of the handpiece. The indicator device may include an audio, visual or other display. The visual display may include a video monitor. The indicator device may include a signal processing circuit responsive to the detector for identifying the presence of steam bubbles in the blood volume of the heart after completion of a transmural channel. The signal processing unit may include a thresholding circuit to determine whether the output from the detector exceeds a predetermined level and the signal processing circuit may include a comparator circuit for comparing the time of the output of the detector with that of the laser firing.

DISCLOSURE OF PREFERRED EMBODIMENT

Other objects, features and advantages will occur to those skilled in the art from the following description of a preferred embodiment and the accompanying drawings, in which.

Figures 1, 2:
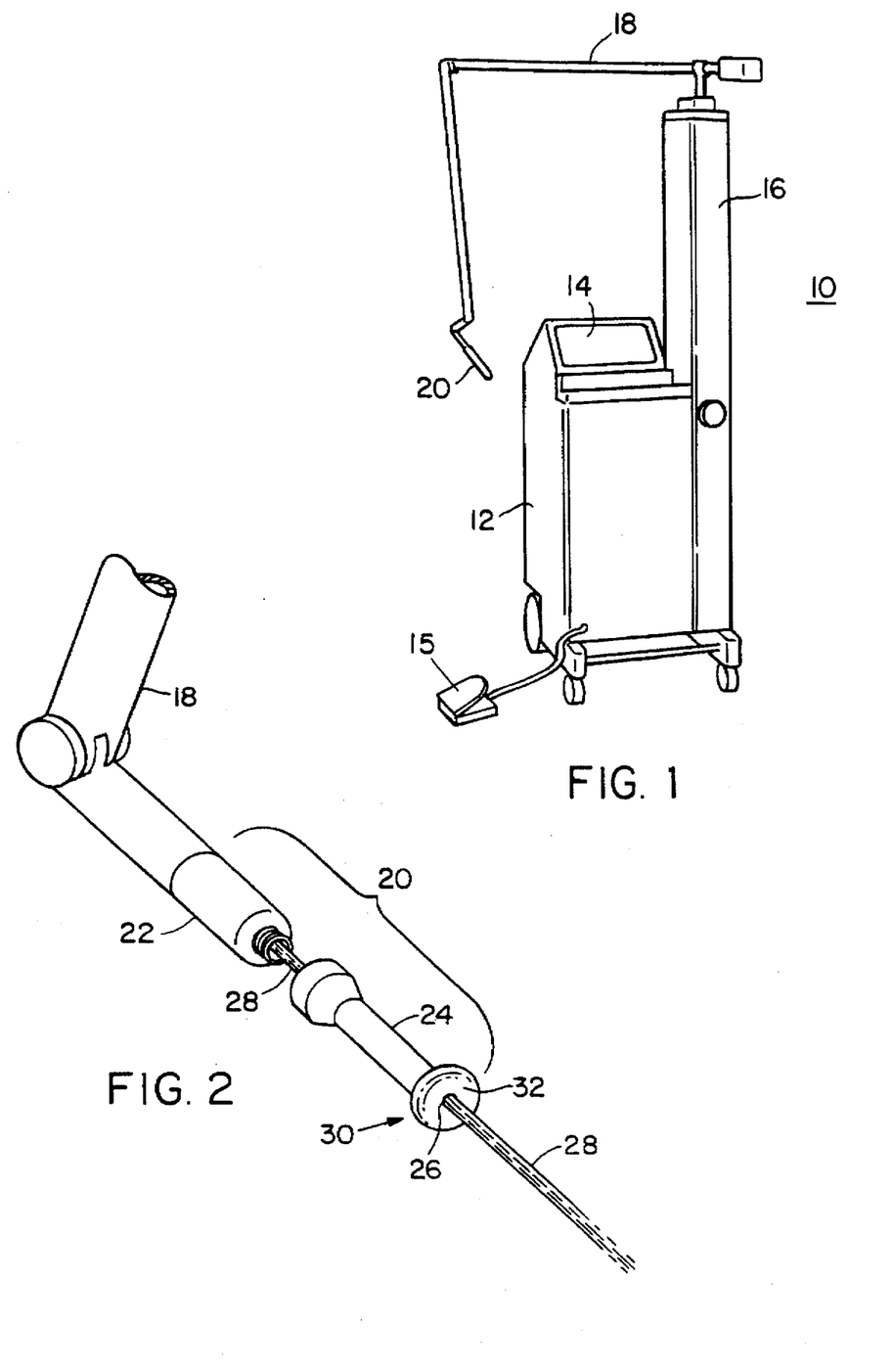
FIG. 1 is a three-dimensional view of a $CO_2$ laser system employing the handpiece of this invention.
FIG. 2 is an enlarged view of a handpiece according to this invention and a portion of the articulated optical arm which carries it.

There is shown in FIG. 1 a surgical laser system 10 including a power supply 12 and control panel 14 for operating $CO_2$ laser 16, whose output beam is directed through articulated arm 18 to a lens unit 22, FIG. 2, including a lens for focusing the laser beam and a barrel 24 which includes an aperture 26 through which the laser beam 28 exits. The distal end 30 of barrel 24 includes an enlarged contact surface 32 for contacting the wall of the heart to be treated by the laser beam. Surface 32 is relatively large to minimize the contact pressure between it and the heart wall, and is flat and smooth with rounded edges. Surface 32 may alternatively have a roughened surface such as lenticular or pyramidical bumps, knurling or textures to enhance gripping action on the heart wall. Surface 32 is typically 1 cm or greater in diameter and may be electrically and thermally insulating.

Figures 3, 4:
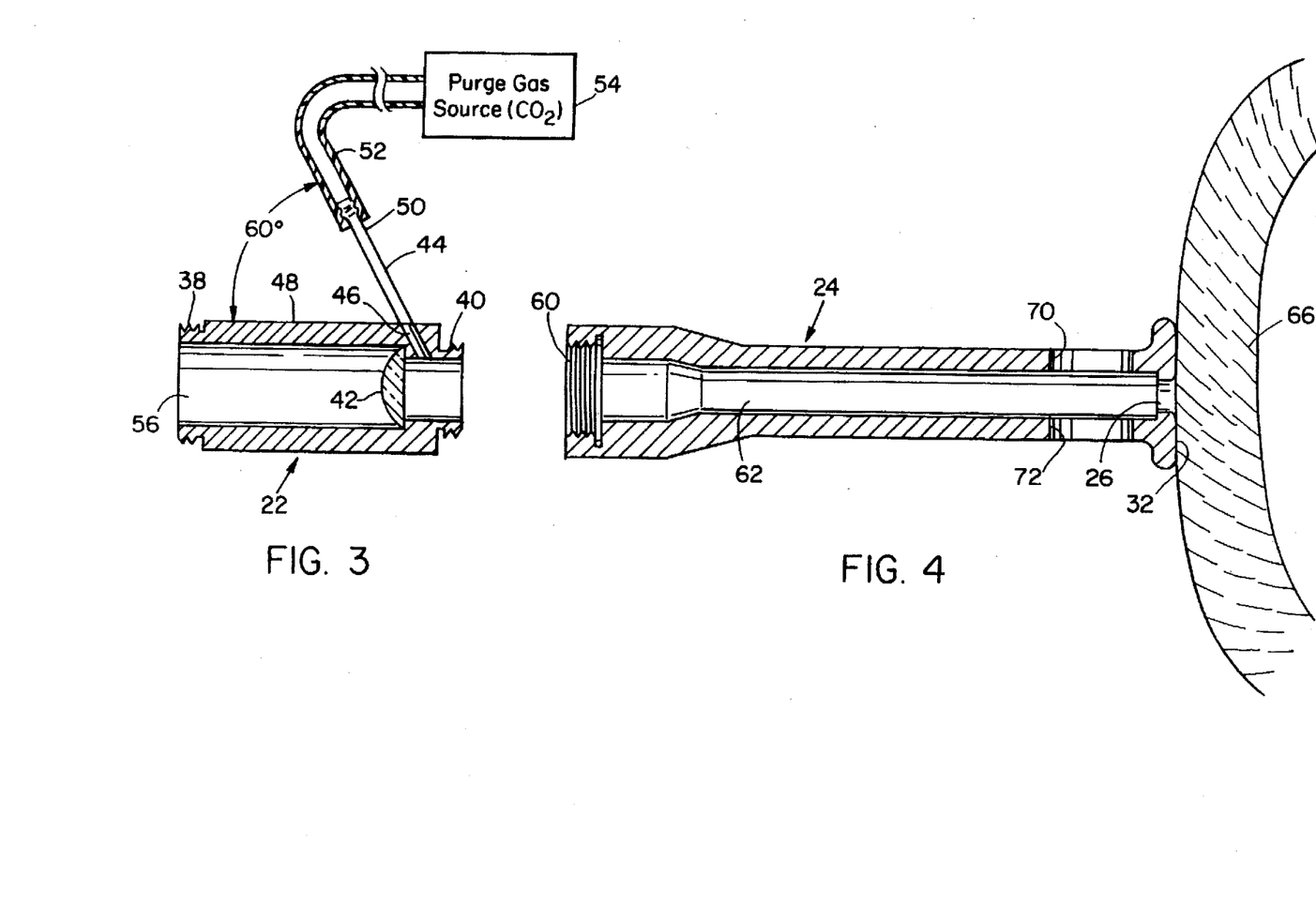
FIG. 3 is an enlarged cross-sectional view of the focusing lens section of the handpiece of FIGS. 1 and 2.
FIG. 4 is an enlarged sectional view of the barrel of the handpiece of FIGS. 1 and 2.

The focusing unit or lens unit 22, FIG. 3, includes a threaded portion 38 for interconnection with arm 18, and a threaded portion 40 which interconnects with barrel 24. Carried within unit 22 is focusing lens 42. An inlet tube 44 is joined by interference fit with bore 46 and a cylindrical wall 48 of unit 22. At its free end 50, inlet 44 is connected to a hose 52 which is in turn connected to a purge gas source 54 which provides a gas such as $CO_2$ under gentle pressure to create a backflow from lens 42 forward into barrel 24. This keeps any debris from the vaporization from contacting and obscuring or damaging lens 42. Lens 42 is positioned directly in line with passage 56 provided in unit 22 for propagation of the laser beam. Threads 40 of lens unit 22 engage with threads 60 of barrel 24, FIG. 4, which also includes a passage 62 which communicates with laser aperture 26 to create a clear passage for the propagation of laser beam 28 to wall 66 of a beating heart. Lens 42 focuses the laser beam proximate aperture 26 and surface 32.

As can be seen clearly in FIG. 4, contact surface 32 is considerably broader than the cross-sectional area of barrel 24 alone and is formed in the shape of a flange with surface 32 being smooth and flat and all the edges rounded. This increases the area of contact with the heart, and therefore decreases the pressure or force per unit area on the heart. It also provides a more stable platform with which to maintain perpendicularity between the beam 28 and the heart wall 66. Barrel 24 includes vent holes 70, 72 for exhausting the purging gas and trapped debris away from the lens 42 and away from aperture 26.

Figure 5:
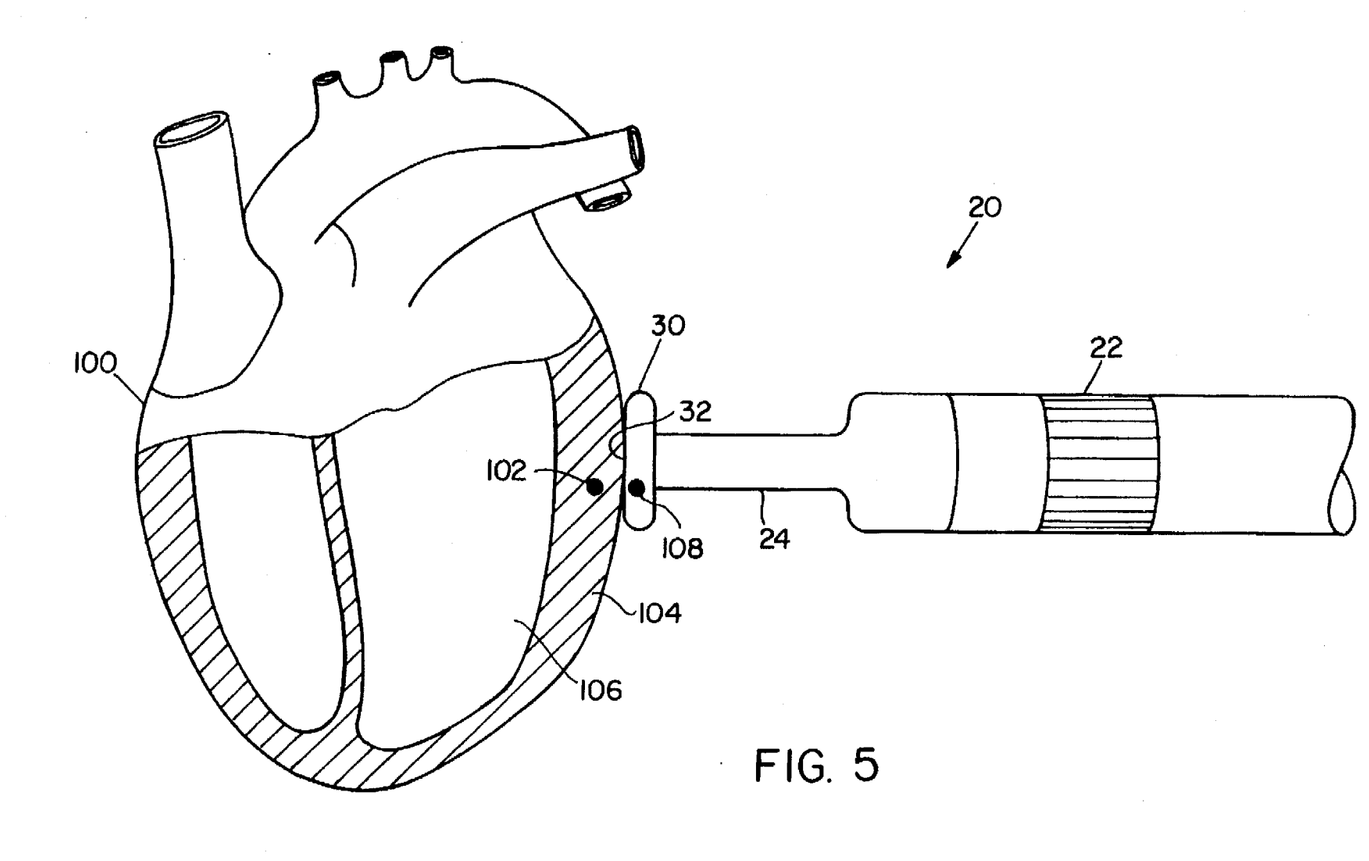
FIG. 5 is a schematic diagram of a handpiece including the ultrasonic detection system according to this invention in contact with the wall of a heart.
Figure 6:
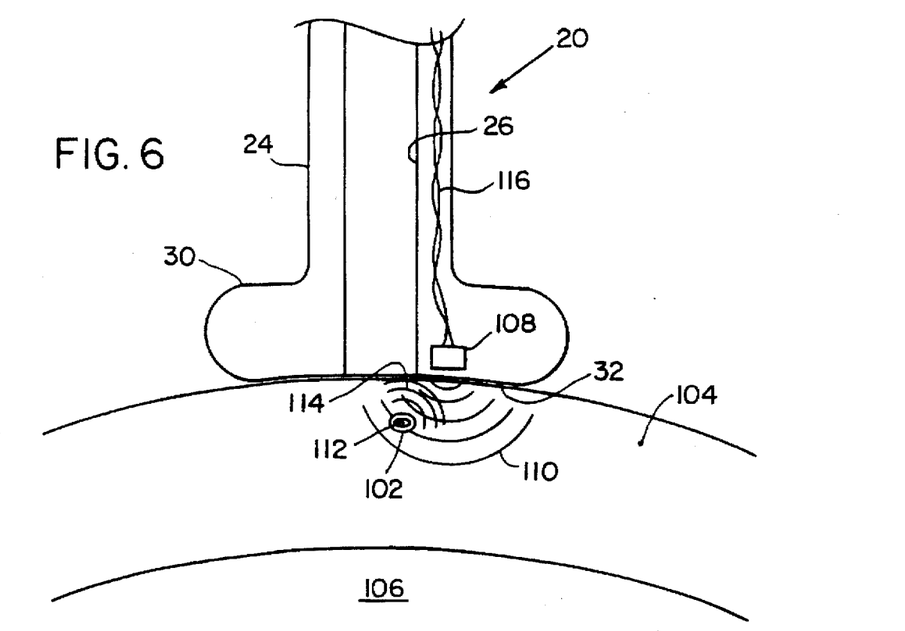
FIG. 6 is an enlarged detailed view of the area of contact of the handpiece and heart of FIG. 5.

There is shown in FIG. 5 a human heart 100 having a coronary vessel 102 in the wall 104 proximate left ventricle 106. An ultrasonic detector 108, shown in phantom, at the distal end 30 of handpiece 20 emits an ultrasonic or acoustic wave 110, as shown in more detail in FIG. 6. Detector 108 is a conventional device such as an AIL-2.5-4-DSC piezo transducer made by Eatalon, Inc., which emits the ultrasonic waves 110 that strike blood vessel 102 and the blood 112 flowing through it. This causes the reflected waves 114 to return to detector 108 and provide an electrical signal representative of that reflection. Cable or wires 116 provide power to energize an ultrasonic crystal in detector 108 and to return the signal to the processing circuits. Detector 108 forms a part of the detection system which also includes the detector circuit 120, FIG. 7, that provides the energy over lines 116 to detector 108 and receives the output signal from detector 108.

Figure 7:
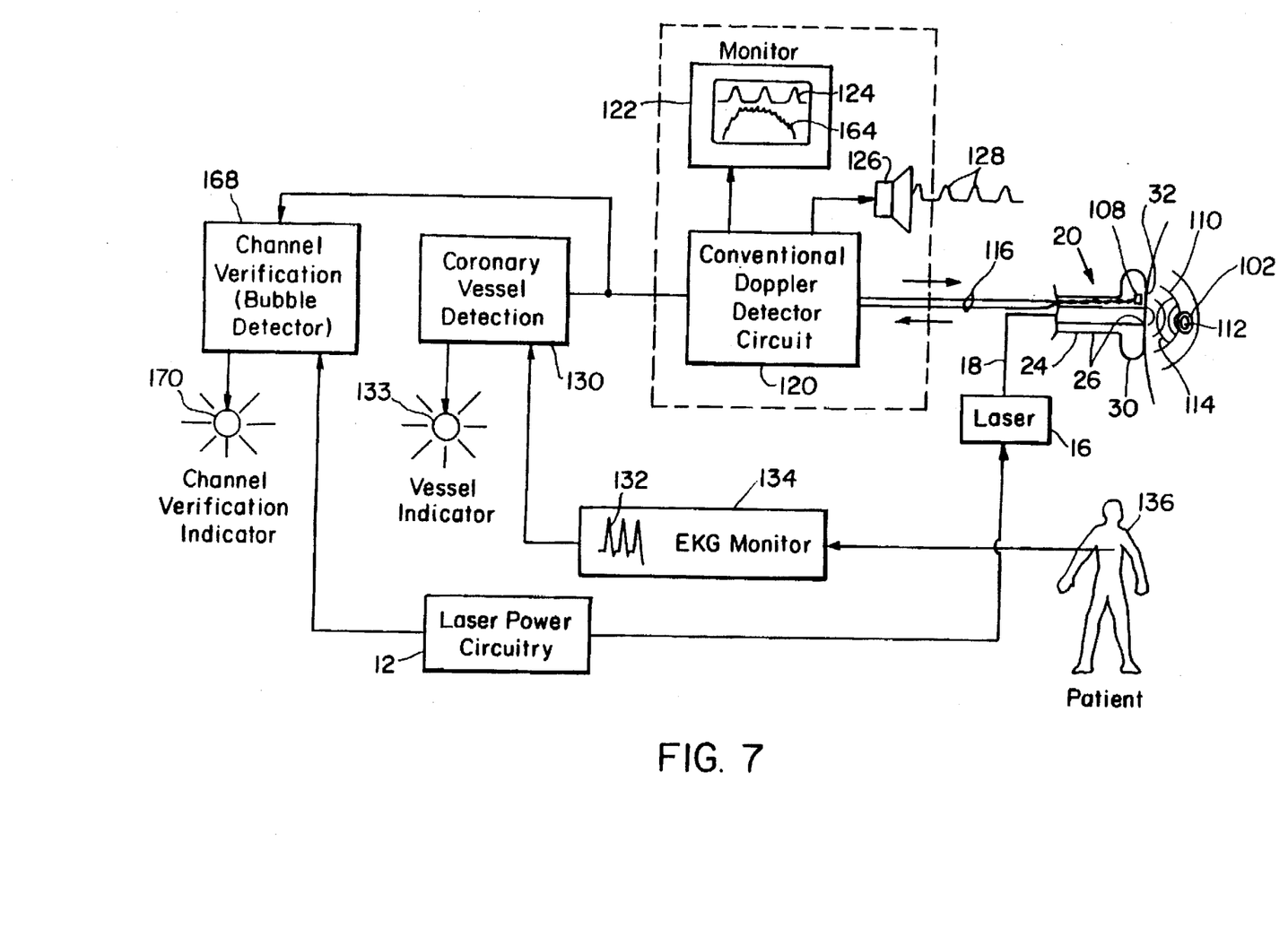
FIG. 7 is a schematic block diagram of an ultrasonic detection system according to this invention used for detection of concealed coronary vessels and for verification of transmural channel completion.

Circuit 120, FIG. 7, operates in a conventional manner to provide a reproduction on monitor 122 of the waveform 124 produced by the pulse in coronary blood vessel 102. Speaker 126 is also provided to emit a series of acoustic notes or beeps 128 which also represent the pulse or heartbeat derived from the blood flowing in coronary blood vessel 102. By listening to the audio output 128 from speaker 126 or viewing the visual waveform on video monitor 122, a surgeon can determine that handpiece 20 is over a blood vessel which is large enough to cause a potential problem and so he will move the handpiece until the audio output 128 or the waveform 124 indicate that the handpiece 20 is no longer hazardously close to the blood vessel 102. Alternatively, or in addition to the indication provided by the representation of waveform 124 on monitor 122 for the interpretation of the surgeon, a more automatic system can be implemented by providing the waveform 124 to coronary vessel detection circuit 130 in conjunction with an EKG signal 132 from EKG monitor 134 connected to the patient 136 whose heart is undergoing transmyocardial revascularization by means of handpiece 20. When the detected waveform correlates with the EKG an indication can be made that a hidden coronary artery is detected. The output from coronary vessel detection circuit 130 may operate audio, visual, or other means to alert the physician that handpiece 20 is too close to a major coronary blood vessel 102. For example, a simple tone generator or a red light 133 could be energized.

Figure 8:
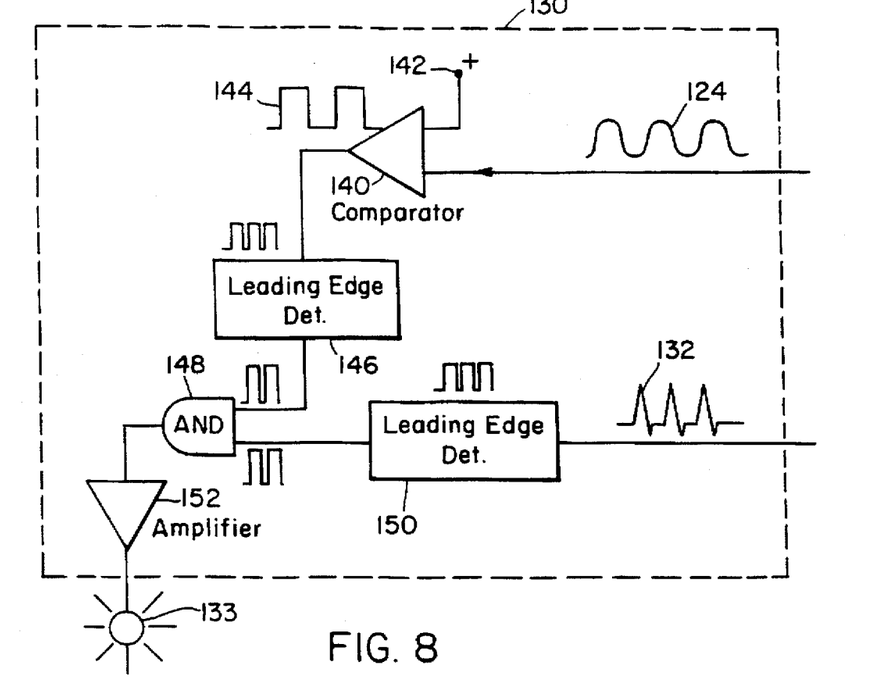
FIG. 8 is a more detailed circuit diagram of the coronary vessel detection circuit of FIG. 7.
Figure 9:
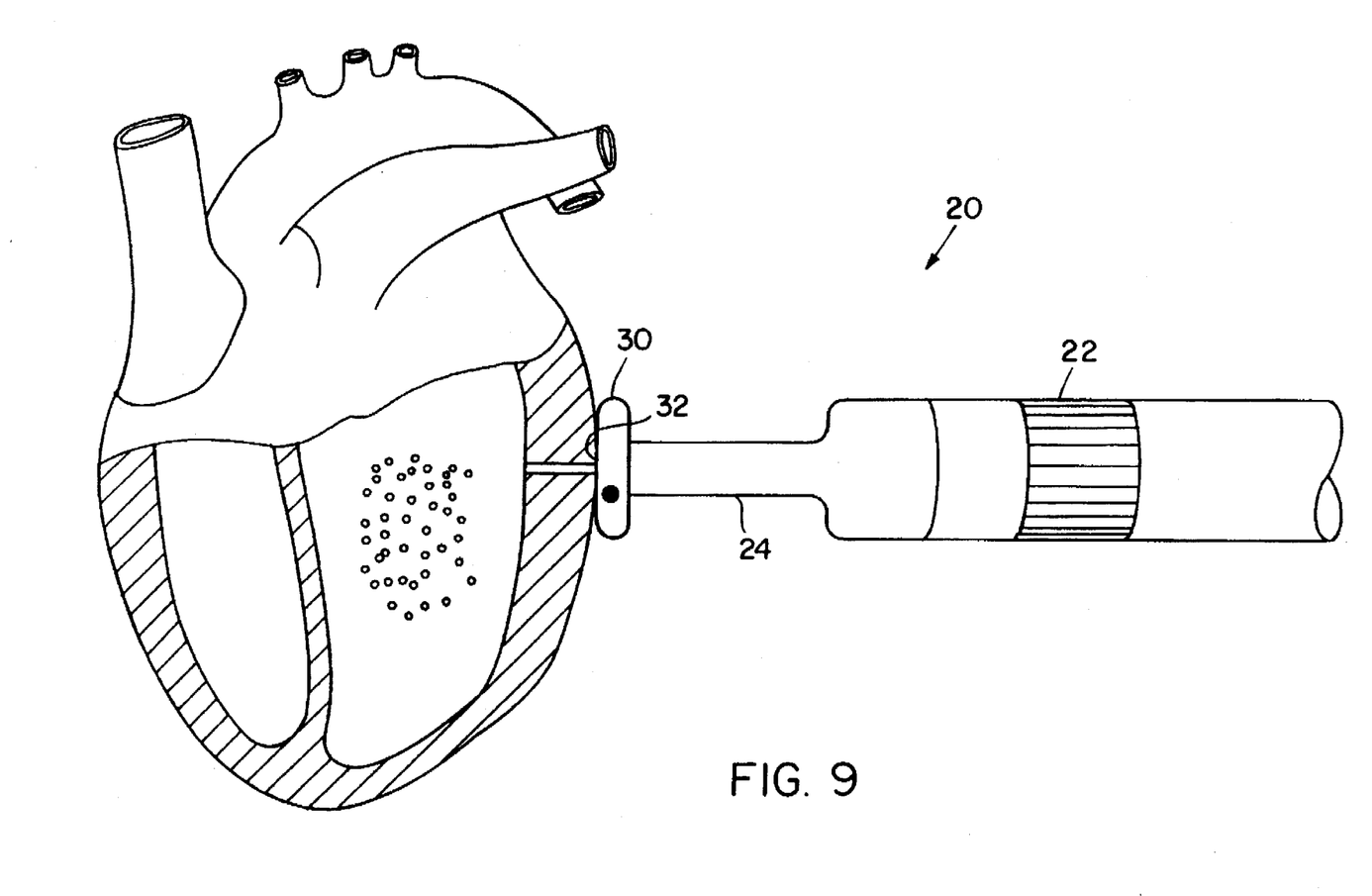
FIG. 9 is a view similar to FIG. 5 illustrating the creation of the steam bubbles upon the completion of a transmural TMR channel in the wall of the heart.

Coronary vessel detection circuit 130 is shown in more detail in FIG. 8 to include a comparator 140 which receives the pulse waveform 124 and compares it to a threshold voltage 142. This provides a square wave 144 which produces a pulse each time the pulses of waveform 124 exceed the threshold provided at 142.

The output from comparator 140 is delivered to a leading edge detection circuit 146 whose output is delivered to AND gate 148. EKG signal 132 from EKG monitor 134 is also delivered to a leading edge detection circuit 150 whose output is also delivered to AND gate 148. The conjunctive occurrence of pulses provided by the leading edge detection circuits 146 and 150 derived from the pulse waveform 124 and EKG waveform 132 cause AND gate 148 to provide an output to amplifier 152 to light indicator tone generator/light 133 or provide some other sort of visual or other indication.

Figure 10:
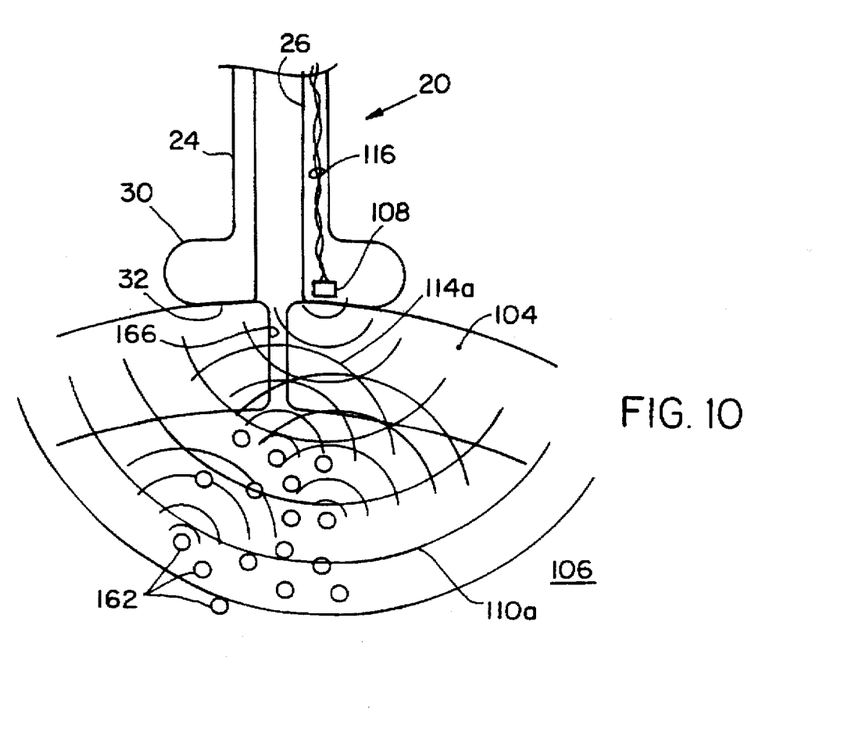
FIG. 10 is an enlarged detailed view of the handpiece, heart and steam bubbles of FIG. 9.

The detection system according to this invention including detector circuit 120 and detector crystal 108 may also be used for detecting verification of a transmural laser created transmyocardial revascularization channel. In a simple embodiment the output from detector crystal 108, FIG. 7, is delivered to detector circuit 120 that provides a waveform to video monitor 122. Normally the waveform will appear as a normal pulse waveform 124. After a channel has been cut through the heart wall using a $CO_2$ laser, a white noise is generated due to reflections from steam bubbles which are generated from the laser energy's interaction with the water from the blood cells and plasma within the ventricle that has been vaporized by the laser energy as shown in FIG. 10, where the outgoing acoustic waves 110a strike steam bubbles 162 and are reflected back 114a to detector 108. The signal thus generated is delivered over cable 116 to detector circuit 120 which provides an output to video monitor 122 in the form of waveform 164, FIGS. 7 and 11. While normally this waveform would appear as heart pulse 124, the effect of the bubbles 162 occurring immediately after transmural channel 166 has been cut through wall 104 produces an enlarged prolonged white noise waveform 164 which is distinguishable from the normal heart pulse waveform 124. The surgeon, upon seeing this waveform immediately after having fired the laser, understands that he has broken through the wall and is seeing the steam bubbles released into the blood in the left ventricle 106. The recognition of this condition can be done electronically by combining the waveform signal 164 from detector circuit 120 in channel verification circuit 168, FIG. 7, with a signal from the laser power circuitry 12 and laser 16 indicating when the laser 16 has fired. When the recognition has been made that the waveform 164 is indeed a reflection from steam bubbles 162, an indicating device such as red light or tone generator 170 may be used as a channel verification indicator.

Figure 11:
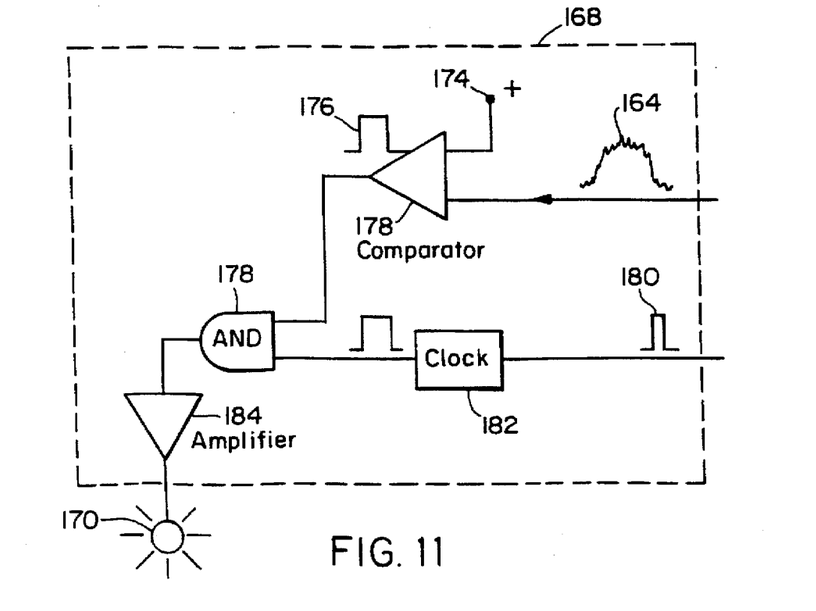
FIG. 11 is a more detailed schematic of the channel verification circuit of FIG. 7.

Channel verification circuit 168 is shown in greater detail in FIG. 11 as including comparator 172 which receives waveform 164 representative of the reflection from the steam bubbles and compares it to the threshold 174. This creates a pulse 176 having a duration as long as a portion of the waveform 164 exceeds the threshold available at 174. The output pulse 176 from comparator 172 is delivered to AND gate 178. Another pulse 180 representing the laser trigger or firing is provided to clock circuit 182 which provides an output for some period of time, for example three to ten seconds, after the occurrence of the pulse 180 indicating the laser triggering. If then a signal having a threshold above a predetermined level occurs for a period within three to ten seconds, for example, after trigger pulse 180, AND gate 178 will provide an output to amplifier 184 to light indicator light 170. The indicator will remain on and indicating as long as the bubbles are sensed during the period after the laser firing. Light/tone generator 170 will remain off if no bubbles are detected or if the laser has not fired.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. An ultrasonic detection system for detecting a concealed coronary blood vessel in transmyocardial revascularization, comprising:

laser means for creating a laser beam;

laser handpiece means, responsive to said laser means, for contacting the wall of a heart and creating a channel therein with said laser beam;

an ultrasonic detector in said handpiece means; and indicator means, responsive to said ultrasonic detector, for indicating the presence of a coronary vessel concealed in the heart wall so that it can be avoided by the laser beam.

2. The ultrasonic detection system of claim 1 in which said detector is mounted in the distal end of said handpiece means.

3. The ultrasonic detection system of claim 1 in which said indicator means includes a visual display.

4. The ultrasonic detection system of claim 3 in which said visual display includes a video monitor.

5. The ultrasonic detection system of claim 1 in which said indicator means includes a signal processing circuit, responsive to said detector, for identifying the presence of a concealed coronary blood vessel.

6. The ultrasonic detection system of claim 5 in which said signal processing circuit includes a thresholding circuit to determine whether the output from said detector exceeds a predetermined level.

7. The ultrasonic detection system of claim 5 in which said signal processing circuit includes comparator means for comparing the periodicity of the detector output with that of the patient's heartbeat.

8. The ultrasonic detection system of claim 7 in which said comparator means includes an EKG device.

9. The ultrasonic detection system of claim 1 in which said indicator means includes an audio device.

10. An ultrasonic detection system for detecting verification of a transmural laser cut transmyocardial revascularization channel, comprising:

laser means for creating a laser beam;

handpiece means responsive to said laser means, for contacting the wall of a heart to cut a transmyocardial revascularization channel therein with the laser beam;

an ultrasonic detector in said handpiece means; and indicator means, responsive to said ultrasonic detector, for detecting the presence of a completed transmural channel created by the laser beam.

11. The ultrasonic detection system of claim 10 in which said detector is mounted in the distal end of said handpiece means.

12. The ultrasonic detection system of claim 10 in which said indicator means includes visual display.

13. The ultrasonic detection system of claim 12 in which said visual display includes a video monitor.

14. The ultrasonic detection system of claim 10 in which said indicator means includes a signal processing circuit, responsive to said detector, for identifying the presence of steam bubbles in the blood volume of the heart after completion of a transmural channel.

15. The ultrasonic detection system of claim 14 in which said signal processing circuit includes a thresholding circuit to determine whether the output from said detector exceeds a predetermined level.

16. The ultrasonic detection system of claim 14 in which said signal processing circuit includes a comparator circuit for comparing the time of the output of the detector with that of the laser firing.

17. The ultrasonic detection system of claim 10 in which said indicator means includes an audio device.

* * * * *